United States Patent [19]
Child et al.

[11] Patent Number: 5,643,196
[45] Date of Patent: Jul. 1, 1997

[54] TAMPON APPLICATOR

[75] Inventors: William M. Child, Monson; Warren Tarr, Turners Falls, both of Mass.

[73] Assignee: Tambrands Inc., White Plains, N.Y.

[21] Appl. No.: 398,142

[22] Filed: Mar. 3, 1995

[51] Int. Cl.$^6$ ........................................ A61F 13/20
[52] U.S. Cl. ...................... 604/14; 604/15; 604/16
[58] Field of Search ............... 604/1–3, 11–18, 604/904

[56] References Cited

U.S. PATENT DOCUMENTS

| | | | |
|---|---|---|---|
| 2,355,917 | 8/1944 | Knight | 128/263 |
| 2,587,717 | 3/1952 | Fourness | 128/263 |
| 2,829,646 | 4/1958 | Kurkjian | 128/263 |
| 3,101,713 | 8/1963 | Sargent | 128/263 |
| 3,124,134 | 3/1964 | Gardner | 604/15 |
| 3,347,234 | 10/1967 | Voss | 604/18 |
| 3,390,671 | 7/1968 | Hildebrand | 128/263 |
| 3,534,737 | 10/1970 | Jones, Sr. | 604/15 |
| 3,696,812 | 10/1972 | Jaycox | 604/18 |
| 4,077,409 | 3/1978 | Murray et al. | 128/285 |
| 4,273,125 | 6/1981 | Sakurai | 128/263 |
| 4,276,881 | 7/1981 | Lilaonitkul | 128/263 |
| 4,286,595 | 9/1981 | Ring | 128/263 |
| 4,291,696 | 9/1981 | Ring | 128/263 |
| 4,411,647 | 10/1983 | Sakurai et al. | 604/16 |
| 4,413,986 | 11/1983 | Jacobs | 604/14 |
| 4,479,791 | 10/1984 | Sprague | 604/14 |
| 4,508,531 | 4/1985 | Whitehead | 604/74 |
| 4,543,086 | 9/1985 | Johnson | 604/11 |
| 4,573,963 | 3/1986 | Sheldon | 604/15 |
| 4,573,964 | 3/1986 | Huffman | 604/15 |
| 4,610,659 | 9/1986 | Friese | 604/11 |
| 4,650,459 | 3/1987 | Sheldon | 604/15 |
| 4,676,773 | 6/1987 | Sheldon | 604/16 |
| 4,699,610 | 10/1987 | Hanano et al. | 604/16 |
| 4,726,805 | 2/1988 | Sanders, III | 604/15 |
| 4,792,326 | 12/1988 | Tews | 604/11 |
| 4,846,802 | 7/1989 | Sanders, III | 604/15 |
| 4,891,042 | 1/1990 | Melvin et al. | 604/18 |
| 4,911,687 | 3/1990 | Stewart et al. | 604/15 |
| 4,921,474 | 5/1990 | Suzuki et al. | 604/18 |
| 4,960,417 | 10/1990 | Tarr, Jr. et al. | 604/15 |
| 5,330,421 | 7/1994 | Tarr et al. | 604/18 |

FOREIGN PATENT DOCUMENTS

| | | |
|---|---|---|
| 0 221 424 | 5/1987 | European Pat. Off. . |
| 0 223 072 | 5/1987 | European Pat. Off. . |
| 1 045 962 | 10/1966 | United Kingdom . |
| 2 033 754 | 5/1980 | United Kingdom . |
| 2 060 396 | 5/1981 | United Kingdom . |
| 2 081 586 | 2/1982 | United Kingdom . |
| 2 120 945 | 12/1983 | United Kingdom . |
| 2 133 695 | 8/1984 | United Kingdom . |
| 2 204 491 | 11/1988 | United Kingdom . |
| 2 220 359 | 1/1990 | United Kingdom . |
| 9413238 | 6/1994 | WIPO ........................ 604/11 |

*Primary Examiner*—John G. Weiss
*Assistant Examiner*—Dennis Ruhl
*Attorney, Agent, or Firm*—Fish & Richardson P.C.

[57] ABSTRACT

An insertion device is provided for inserting material having an enlarged head portion into a body cavity. The insertion device includes an elongate, tubular holder, shaped for insertion into the body cavity and having an expulsion end which is dimensioned to fit over the head portion of the material and adapted to open to allow the material to be expelled therethrough; an elongate, tubular plunger, adapted to hold telescopically at least a portion of the material to be inserted, dimensioned to fit telescopically and slidably within the holder and to be movable from a telescoped position within the holder to an extended position in which one distal end of the plunger is withdrawn from the distal holder, and adapted, in the extended position, to expel the material from the device when pushed manually into the holder; and a retaining structure, interposed between the plunger and the holder and disposed at the expulsion end to engage the head portion of the material and prevent it from moving with the plunger when the plunger is moved from the telescoped to the extended position. The tubular material holder is a convolutely wound cylindrical tube, and the retaining structure is a convolutely wound cylindrical tube coaxially disposed within the tubular material holder and formed from the same blank as the tubular material holder so that the retaining structure is unitary with the tubular material holder.

16 Claims, 6 Drawing Sheets

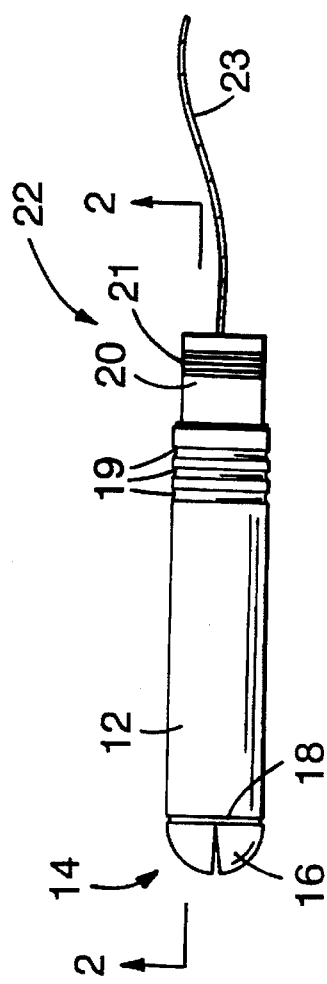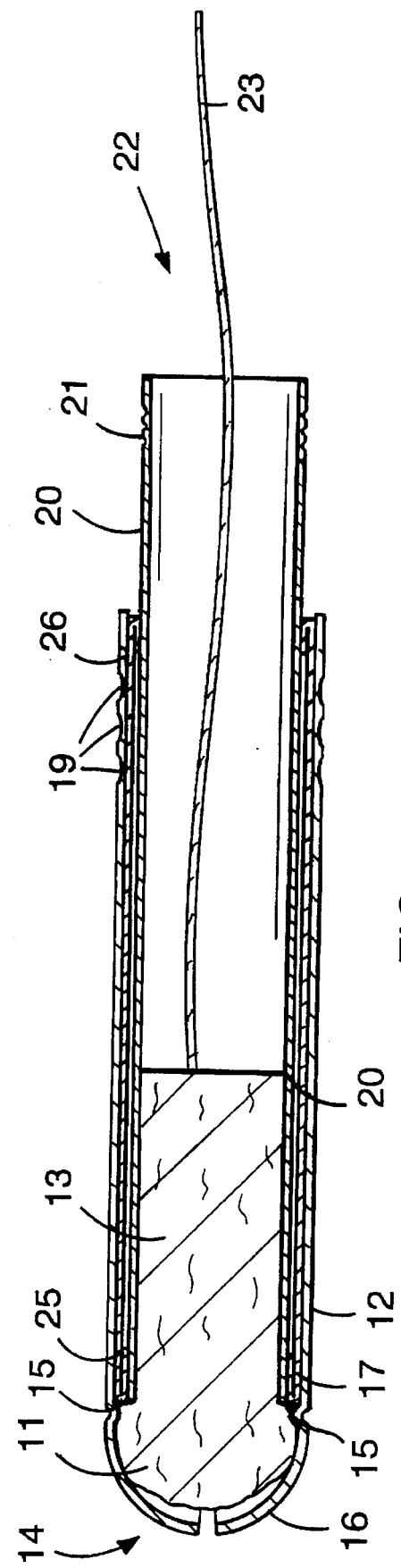
FIG. 1
FIG. 2

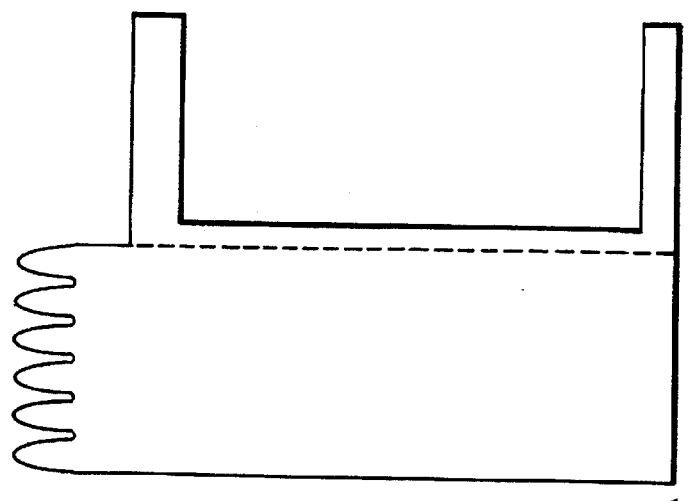
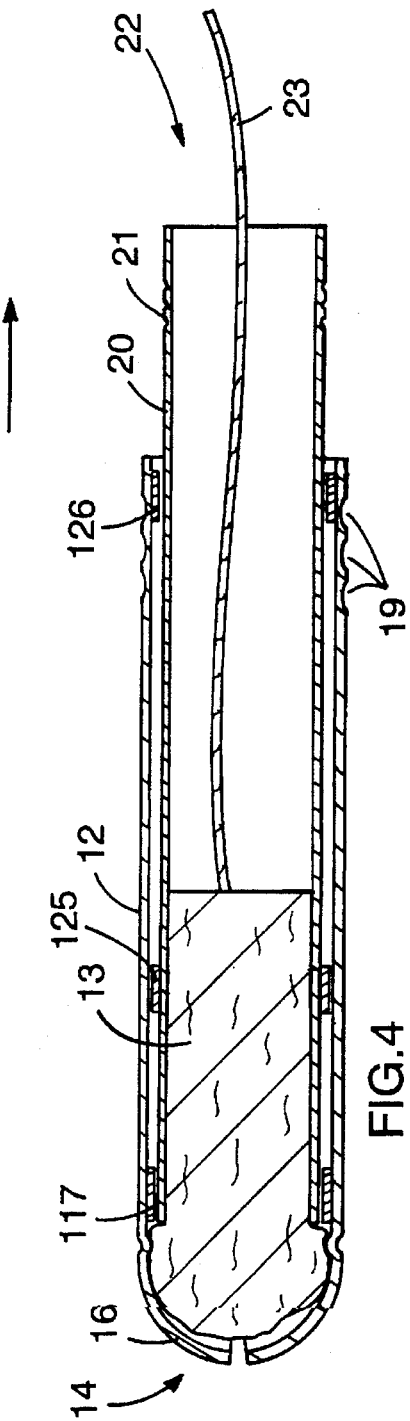

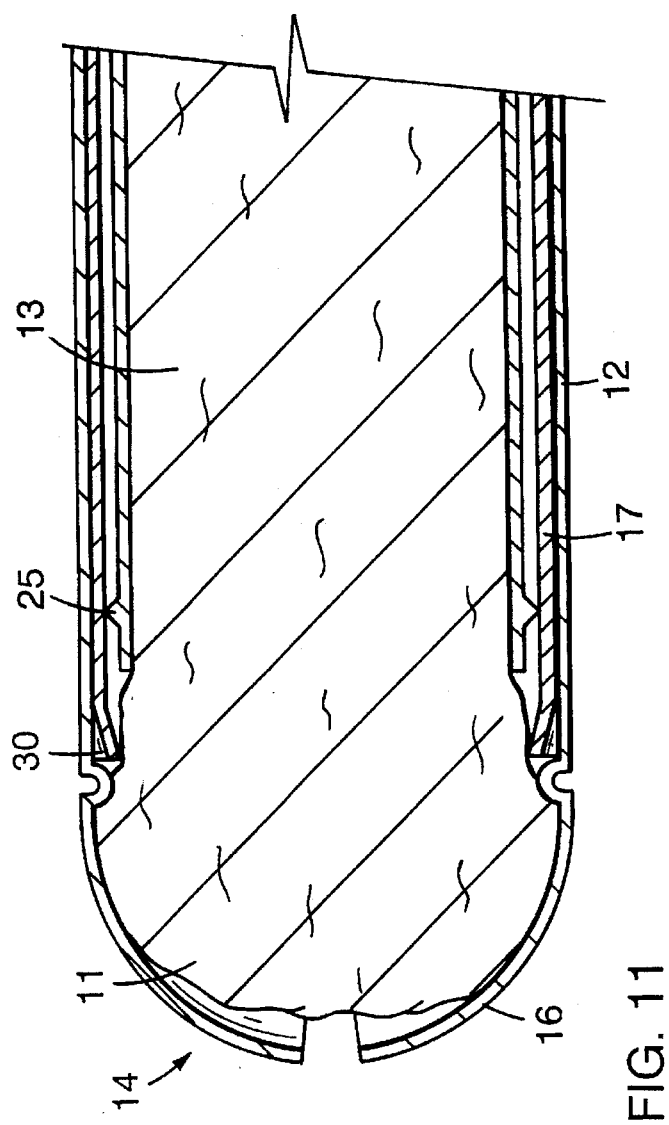
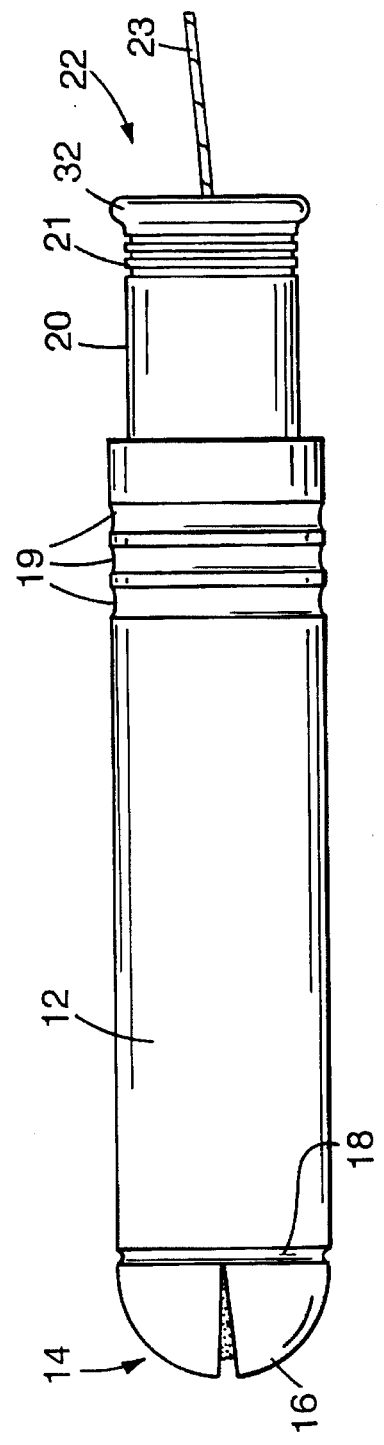
FIG. 11
FIG. 12

TAMPON APPLICATOR

BACKGROUND OF THE INVENTION

This invention relates to a compact insertion device, e.g., a tampon applicator, formed from a paper laminate.

Tampon applicators comprising a pair of telescopically arranged tubes are long known in the art. Some applicators have the tampon exposed at the end intended for vaginal insertion (the expulsion end), while others provide a rounded expulsion end, with the tampon covered by a plurality of "petals" which open during tampon expulsion.

Typically, these applicators comprise a tampon holder tube and a plunger tube, telescopically disposed so that a small portion of the plunger tube is within the holder tube. Such an applicator is thus relatively long, typically about twice the length of the tampon holder tube.

Efforts have been undertaken in the industry to produce a shorter applicator, which would be, e.g., easier to store and transport. Shorter applicators, known in the field as "compact" applicators, are generally formed by disposing most of the length of the plunger tube between the tampon holder tube and the tampon. The plunger tube is withdrawn from the holder tube by the user, prior to insertion. It is thus necessary that the tampon be retained in the holder tube and not withdrawn with the plunger tube. Typically, in closed end applicators this is achieved by a plurality of slots and/or tabs extending from the inner surface of the tampon holder tube to engage the periphery of the "head" of the tampon, thus retaining it in the holder tube. In open end applicators, the head of the tampon itself engages the holder tube and retains the tampon. The provision of slots or tabs for retaining the tampon is disadvantageous, as these structures are difficult to form in paper laminates, which are preferred materials for tampon applicators due to their flushability and biodegradability. Further, in order to form tabs in a paper applicator, it is typically necessary to leave holes, which weaken the applicator and give it an unappealing, flimsy appearance.

U.S. Pat. No. 5,330,421 discloses a compact tampon applicator having a retaining structure for retaining the tampon. The retaining structure is, e.g., a cylindrical tube or ring, separate from the outer holder tube, adhered to the inner surface of the outer holder tube.

SUMMARY OF THE INVENTION

As disclosed in U.S. Pat. No. 5,330,421, a compact type laminated paper insertion device, comprising a tubular material holder and a tubular plunger telescopically disposed in the holder and containing the material to be inserted, can be greatly improved in a variety of respects by providing a retaining structure interposed between the inner wall of the material holder and the outer wall of the plunger. The inventors have now found that the retaining structure can easily and economically be provided by fabricating the tubular material holder as a convolutely wound cylindrical tube, and the retaining structure as a convolutely wound cylindrical tube coaxially disposed within the tubular material holder and formed from the same blank as the tubular material holder so that the retaining structure is unitary with the tubular material holder. This type of retaining structure is also advantageous because it does not need to be adhered to the inner surface of the tubular material holder, and because it is not subject to becoming detached therefrom during manufacture or use of the applicator.

Broadly, the invention features an insertion device for inserting material into a body cavity. The device includes an elongate tubular holder, shaped for insertion into the body cavity and having an expulsion end which is adapted to allow the material to be expelled therethrough; an elongate, tubular plunger, adapted to hold telescopically at least a portion of the material to be inserted, dimensioned to fit telescopically and slidably within a portion of the holder; and a retaining structure, disposed within the tubular holder. As noted above, advantageously the tubular material holder comprises a convolutely wound cylindrical tube, and the retaining structure comprises a convolutely wound cylindrical tube coaxially disposed within the tubular material holder and formed from the same blank as the tubular material holder so that the retaining structure is unitary with the tubular material holder.

In preferred embodiments, the insertion device is a tampon applicator and the material is a tampon having an enlarged head portion. More specifically, preferred tampon applicators are "compact" applicators, discussed in the Background of the Invention, although the invention may be used with other types of applicators.

In one preferred embodiment, at least a portion of the retaining structure is disposed at the expulsion end of the tubular holder to engage the head portion of the material and prevent it from moving with the plunger when the plunger is moved from the telescoped to the extended position. Prior to use, the plunger is retained within the holder, with only a small portion of its distal end extending outside of the holder tube. The material to be inserted (e.g., a tampon) is retained within the plunger, and has a swelled head portion which extends over, and engages, the retaining structure. When the applicator is to be used, the user pulls the plunger back to an extended position, in which it is positioned to expel the tampon when reinserted into the applicator. By engaging the head of the tampon, the retaining structure thus retains the tampon securely in place while the plunger is being pulled to the extended position.

In another preferred embodiment, or as an additional feature in the above embodiment in which the retaining structure retains the head portion, the retaining structure comprises a stop near the distal end of the tubular holder and the plunger has a raised area at its expulsion end positioned and dimensioned to interlock with the stop to resist withdrawal of the tubular plunger from the tubular holder.

In other preferred embodiments, the retaining structure is a tube which extends for approximately the length of the holder, i.e., from the base of the head of the material to be inserted to the distal end of the holder.

Preferably, either the holder or the retaining tube has a stop, or locking ring, on its inner surface, disposed at the distal end of the holder tube, and the plunger has a corresponding raised area, e.g. ring or c-shaped segment, at its expulsion end, such that the stop and raised area interlock to retain the plunger tube within the holder tube when it is withdrawn prior to use.

In other embodiments, the retaining structure is a tube having a shorter length than the tubular material holder, e.g., a ring disposed adjacent the head of the tampon to retain the tampon when the plunger tube is withdrawn. In this embodiment, the stop which retains the plunger may be a second ring disposed at the distal end of the tampon holder tube. A third ring is preferably formed as a part of or adhered to the plunger, disposed at or distally of its expulsion end, forming the locking ring which interlocks with the stop. The third ring is located such that the plunger can be withdrawn far enough to completely clear the tampon and pushed forward enough to ensure complete expulsion of the tampon.

In another aspect, the invention features an insertion device for inserting material into a body cavity, including an elongate, tubular holder, shaped for insertion into the body cavity and having an expulsion end from which the material is expelled, and an elongate, tubular plunger, adapted to hold telescopically at least a portion of the material to be inserted. A portion of the distal end of the holder is folded under, and the plunger includes a plurality of petals at its proximal end, at least one of which is folded back for engagement with the folded under portion, to retain the plunger tube within the holder tube.

Advantageously, the applicators of the device may be completely formed from paper laminate, without the need to form slots or tabs which weaken the applicator and give it an unattractive appearance.

The invention also features methods of manufacturing the tampon applicators of the invention.

The term "distal end" as used herein, refers to the end of each element which is opposite the expulsion end.

The term "convolutely wound", as used herein, refers to a manner of cardboard tube manufacture in which a flat blank is rolled, starting at a first edge, so that when the blank is completely rolled the opposite edge of the blank is disposed substantially parallel to the first edge (assuming that the first and opposite edges of the blank were initially substantially parallel).

Other features of the invention will be apparent from the following description of preferred embodiments and from the claims.

BRIEF DESCRIPTION OF THE DRAWINGS

FIG. 1 shows a compact tampon applicator according to one embodiment of the invention.

FIG. 2 shows a side cross-sectional view of the applicator of FIG. 1, enlarged to show detail.

FIG. 3 shows a side cross-sectional view of the applicator of FIG. 1 with the plunger in its extended position.

FIG. 4 is a partial cross-sectional side view of a compact tampon applicator according to an alternate embodiment of the invention. FIG. 4A is a front plan view of a blank used to form a plunger tube for use in this embodiment.

FIG. 8A is a front plan view of a blank used to form a holder tube and retaining tube according to another alternative embodiment of a holder tube and retaining tube formed using the blank of the invention. FIG. 8B is a schematic perspective view of FIGS. 8 or 8A.

FIG. 11 is a cross-sectional side view of a portion of a compact applicator according to another alternate embodiment of the invention.

FIG. 12 is a side view of a compact applicator according to another alternate embodiment of the invention.

DESCRIPTION OF THE PREFERRED EMBODIMENTS

Figure 5:
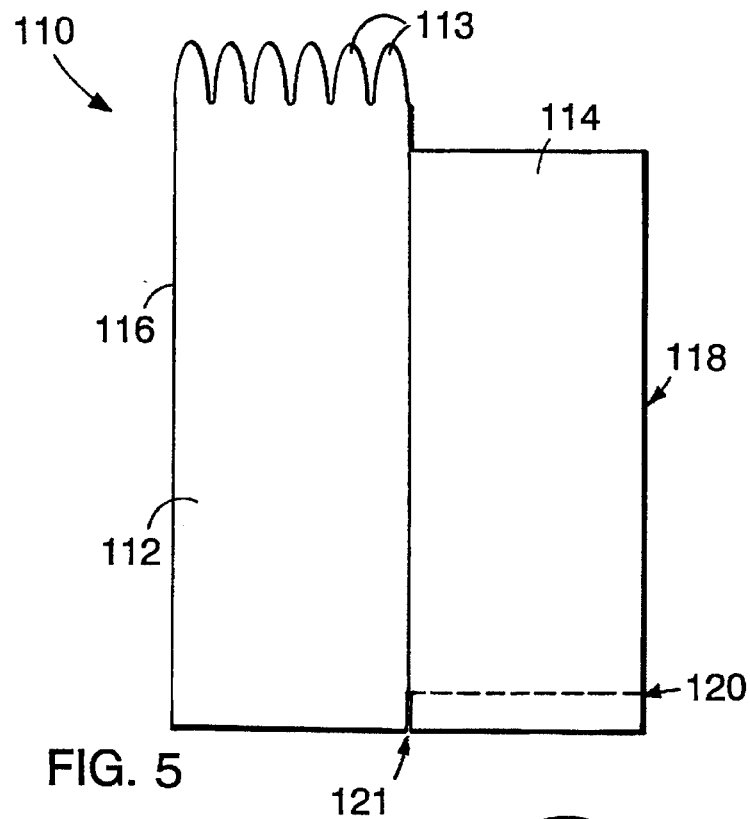
FIG. 5 is a front plan view of a blank used to form a holder tube and retaining tube according to the embodiment of the invention shown in FIGS. 1 and 2.

An applicator according to a preferred embodiment of the invention is shown in FIGS. 1–3. The applicator comprises tubular tampon holder 12, retaining tube 17, and plunger 20, telescopically and slidably mounted inside of retaining tube 17. Tampon 13 is retained within plunger 20, with its head 11 extending over and engaging edge 15 of retaining tube 17, so that when plunger 20 is pulled back tampon 13 will remain in place. Tampon withdrawal cord 23 extends out of distal end 22 of the applicator. Expulsion end 14 of holder 12 comprises a plurality of petals 16. Preformed hinge or groove 18 is disposed circumferentially at the base of the petals. Circumferential indentations 19 and 21 are embossed into holder 12 and plunger 20, respectively, at their distal ends, to provide gripping surfaces for the user. These indentations are typically relatively shallow. Alternatively, the gripping surface may comprise raised formations, such as those described in U.S. Pat. No. 5,346,468, issued Sep. 13, 1994, the disclosure of which is hereby incorporated by reference.

FIG. 3 illustrates the applicator in its extended position, subsequent to the user withdrawing plunger 20 to its extended portion, and prior to reinsertion of the plunger 20 to expel tampon 13. One problem which may occur during reinsertion of the plunger is "repositioning", i.e. the plunger sliding back over the tampon instead of engaging the distal end of the tampon to expel it. This problem may be solved by providing petals on the plunger tube, which close up when the plunger tube is pulled back and removed from around the tampon; by slightly flaring the distal end of the tampon during compression so that the plunger cannot easily slide over the flared end; by a tab or protrusion in a small area of the retaining structure which would force the plunger and/or tampon slightly off center; or by a small diameter plunger. Other methods could also be used.

As shown in FIG. 3, inadvertent removal of the plunger from the applicator can be avoided by providing a plunger 220 having petals 222 and 222a. (These petals also prevent repositioning.) While petals 222 remain in their normal position, to prevent repositioning, alternating petals 222a are bent back, so that they engage a folded-under portion 224 of retaining tube 217. This means of retaining the plunger within the holder may be used in other types of compact and standard tampon applicators, in addition to the applicators described herein. Other means of retaining the plunger can be used, but preferably the interlock provided is sufficient to withstand the force created by the user pulling the plunger back. The plunger of the compact applicator is much more likely to come out than a non-compact plunger, which is not typically pulled back, so it is preferred to provide a more positive interlock than is generally provided in non-compact applicators.

FIG. 4 shows an alternate embodiment of the invention, in which retaining tube 17 is replaced by retaining ring 117. As with retaining tube 17, retaining ring 117 is formed from the same blank as the outer tube. The ring may be any desired length, with about 0.125 to 0.375 inches being preferred. Instead of a complete ring, as shown, the retaining structure may be a C-shaped member (an open ring), formed from the same blank as the outer tube. The use of a retaining ring, or C-shaped member, in place of a retaining tube requires less paper, but may make the applicator more difficult to manufacture.

Also as shown in FIG. 4, rings may be adhered onto plunger 20, distally of its expulsion end, preferably about 0.625" from the expulsion end, and near the distal end of holder 12 to provide the interlocking of the plunger and the holder. In FIG. 4, locking ring 126 and raised ring 125 replace the locking means shown in FIG. 3. Preferably, rather than adhering separate rings onto the plunger tube, the raised ring is formed by convolutely winding the plunger tube from the blank shown in FIG. 4A, rolling the tube in the direction indicated by the arrow.

FIG. 5 shows a blank 110 which is suitable for forming the holder tube and retaining tube portions of the applicator shown in FIGS. 13. Blank 110 includes a first portion 112, for forming the tampon holder tube 12, and a second portion 114, for forming the retaining tube 17. First portion 112 includes a plurality of curved segments 113, which will be formed during manufacturing into the petals 16 of the tampon holder tube. The first and second portions have side edges 116 and 118, respectively. Second portion 114 includes a score line 120 and a cut 121, disposed near what will be the distal end of the tubes.

Figure 6:
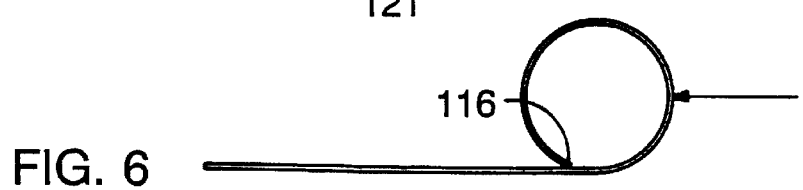
FIG. 6 is an end view showing the manner in which the blank of FIG. 5 is rolled to form the holder tube and retaining tube.

A tampon holder tube and retaining tube are formed from the blank shown in FIG. 5 by rolling the blank, starting at edge 118, as shown in FIG. 6. When the blank is completely rolled, edge 116 is sealed against the outer surface of the tampon holder tube 12 by any suitable technique. Preferably sealing is accomplished using a water-soluble or water-degradable adhesive. When the second portion of the tube is rolled, the distal portion of the blank folds up at the score line 120, assisted by cut 121, creating folded-under portion 224 shown in FIG. 3.

Figure 7:
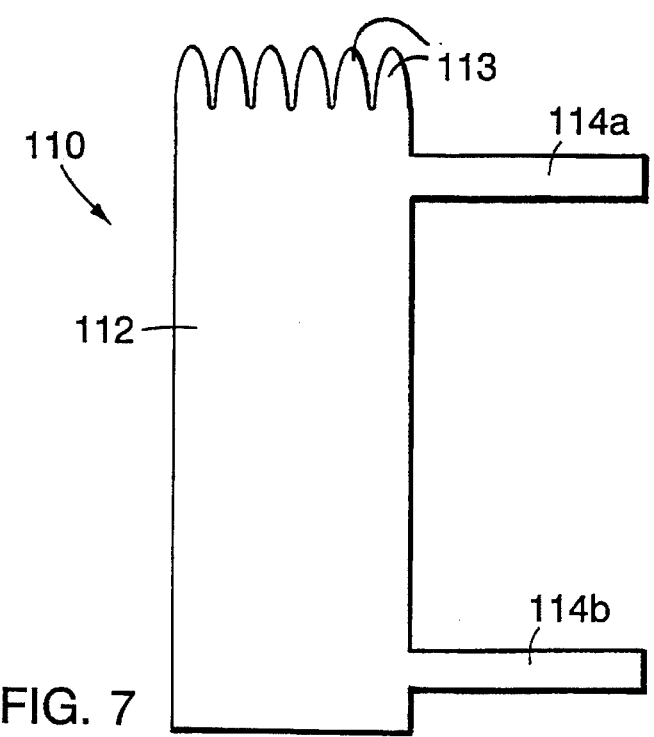
FIG. 7 is a front plan view of a blank used to form a holder tube and retaining tube according to an alternative embodiment of the invention.

A blank according to an alternative embodiment of the invention is shown in FIG. 7. In this embodiment, the blank includes a first portion 112 for forming the tampon holder tube, and a pair of second portions 114a, 114b for forming the ring-shaped retaining and locking structures 117 and 126 shown in FIG. 4. As mentioned above, these structures need not be complete rings, but could instead be C-shaped members. If C-shaped members are used, it may be necessary to adhere the C-shaped member to the inside of the holder tube, or make the blank from a stiff cardboard laminate. Whether complete rings or C-shaped members are formed can be easily determined by selecting a desired length for portions 114a, 114b.

The tampon may be any radially or axially compressed tampon having a swelled "head" area.

It is preferred, for complete flushability and biodegradability, that the tampon holder/retaining tube and the plunger are both made of laminated paper. However, if desired, either of the tubes may be of a different material, e.g. a conventional thermoplastic or a water soluble polymer, such as the water soluble modified polyvinyl alcohol commercially available from Air Products, Allentown, Pa., under the tradename VINEX. If a plastic material is used to form the blank for the holder tube/ retaining tube, it should be thin and/or flexible enough to be easily rolled. The laminated paper used in the holder tube and plunger tube is preferably a laminate of groundwood paper, for economy, with an outer layer of bleached Kraft or other white paper, for aesthetic purposes. The portion of the blank which forms the retaining tube need not include this outer layer, if it is desired to omit it, because the resulting retaining tube is not visible to the consumer. The outer surface of the tube may have a coating disposed thereon to provide improved water resistance, slip and aesthetic characteristics. This coating may be a wax coating, as is known in the art. Alternatively, an outer polymer layer (e.g., cellophane) may be laminated on the outside of the paper layers, as disclosed in U.S. Pat. No. 5,346,468, incorporated hereinabove by reference. If such a laminated polymer layer is used, the improved finger grip formations described in the same U.S. patent may be provided on the holder tube.

The blank used to form the holder tube and retaining tube is preferably cut or punched from a paper or cardboard laminate which includes 1 to 3 plys of paper, preferably two plys, and has a thickness of from about 0.2 mm to 0.6 mm, more preferably about 0.35 mm. The outer surface of the plunger is preferably spaced from the inner surface of the retaining tube by about 0.3 mm to 0.5 mm.

While preferred embodiments have been described above, other variations and modifications are within the scope of the following claims.

Figure 8:
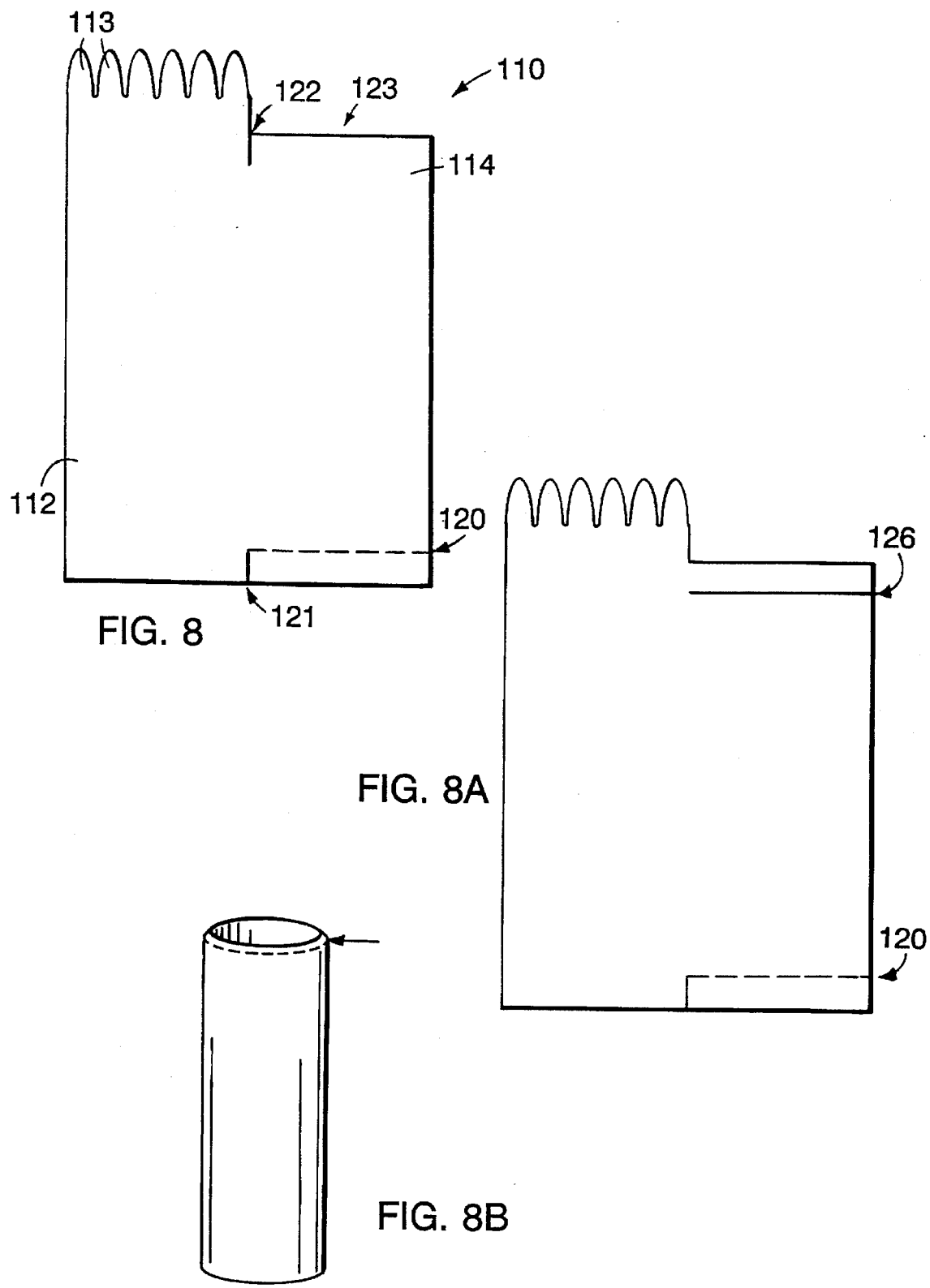
FIG. 8 is a front plan view of a blank used to form a holder tube and retaining tube according to another alternative embodiment of the invention.

A blank according to yet another embodiment of the invention is shown in FIG. 8. In this embodiment, a cut 122 is provided at the intersection of the first and second portions of the blank, at the proximal edge 123 of the blank. Cut 122 allows the region of the second portion of the blank which is closest to the head of the tampon to roll inward as the tube is rolled up (FIG. 6), thereby improving the retention of the tampon by the retaining tube. Alternatively, as shown in FIG. 8A, the blank may be provided with a score line 126 to accomplish the same purpose. Optionally, the blank can be provided with both a cut and a score line, e.g., if the cardboard laminate used is particularly stiff. The resulting retaining tube, having an in-rolled proximal end, is shown in FIG. 8B, in which the tampon holder tube has been omitted for clarity.

Figure 9:
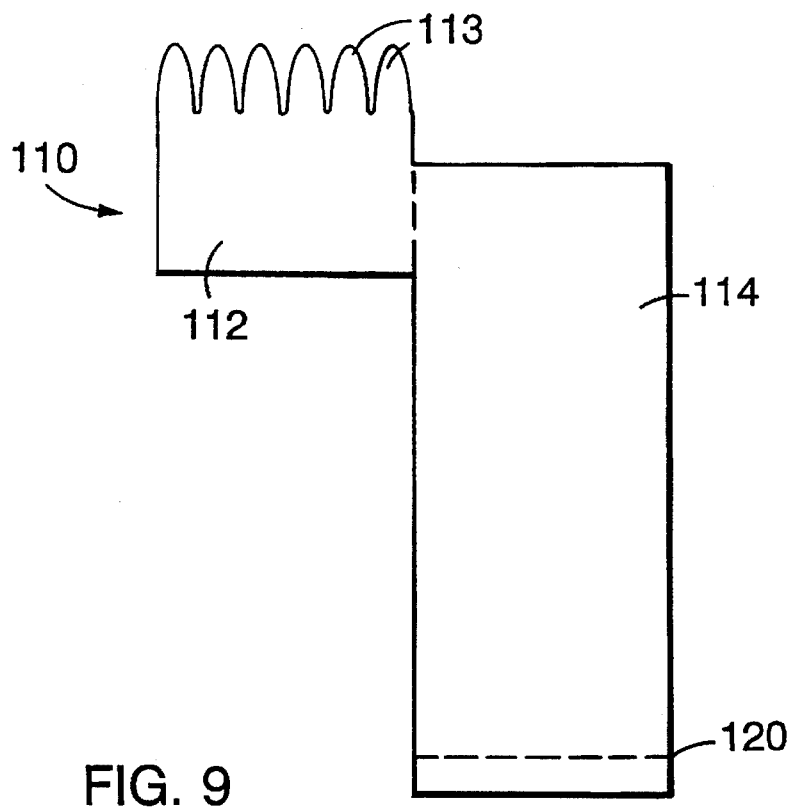
FIG. 9 is a front plan view of a blank used to form a holder tube and retaining tube according to yet another alternative embodiment of the invention.

In another alternative embodiment, the retaining tube may be longer than the holder tube, if the first and second portions of the blank are cut accordingly, e.g., as shown in FIG. 9.

Figure 10:
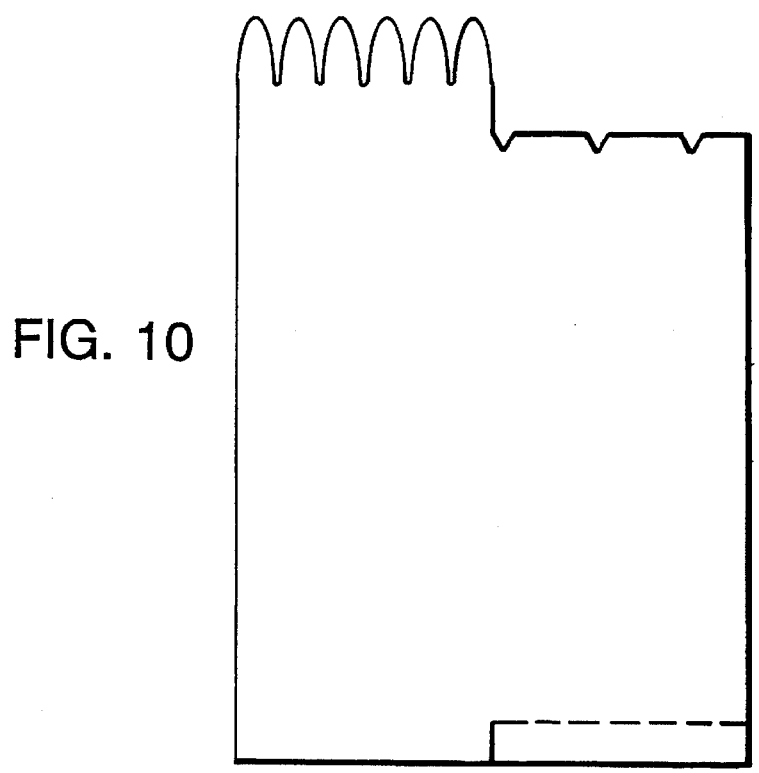
FIG. 10. is a front plan view of a blank used to form a holder tube and retaining tube according to yet another alternative embodiment of the invention.

As shown in FIGS. 10 and 11, crimps 30 may be formed in retaining tube 17 by forming v-shaped notches in the retaining tube portion of the blank. These crimps will enable the retaining tube to more positively retain the tampon in place when the plunger tube is pulled back. Any number of crimps may be used; 3 crimps at 120 degree intervals or 4 crimps at 90 degree intervals (as shown) are preferred.

As shown in FIG. 12, the distal end of the plunger tube may include a rim 32, preferably formed by curling the paper laminate outwardly. This smooth rim provides a more positive finger grip for the user.

Many other variations will be apparent to those skilled in the art.

We claim:

1. An insertion device for inserting material into a body cavity, comprising:

an elongate tubular holder, shaped for insertion into the body cavity and having an expulsion end which is adapted to allow said material to be expelled therethrough and a second end opposite the expulsion end;

an elongate tubular plunger, adapted to hold telescopically at least a portion of the material to be inserted, dimensioned to fit telescopically and slidably within a portion of said holder, and having a first end for contacting the material and a second end providing a finger grip; and a retaining structure, disposed within said tubular holder;

wherein the tubular holder comprises a convolutely wound cylindrical tube, and the retaining structure comprises a convolutely wound cylindrical tube coaxially disposed within the tubular holder, and wherein the tubular holder and retaining structure are integral unsevered portions of the same piece of material.

2. The device of claim 1 wherein said plunger is dimensioned so that a major portion of the plunger fits telescopically within the tubular holder and the plunger is movable from a telescoped position within said holder to an extended position in which the second end of the plunger is withdrawn from the holder, and the tubular plunger is adapted, in said extended position, to expel said material from said device when pushed manually into said tubular holder.

3. The device of claim 2 wherein said material has an enlarged head portion and at least a portion of said retaining structure is disposed at said expulsion end of said tubular holder to engage the head portion of said material and prevent it from moving with said plunger when said plunger is moved from said telescoped to said extended position.

4. The device of claim 1 or 3 wherein said retaining structure comprises a stop near the second end of said tubular holder.

5. The device of claim 4 wherein the plunger has a raised area at its expulsion end positioned and dimensioned to interlock with said stop to resist withdrawal of the tubular plunger from the tubular holder.

6. The device of claim 1 wherein said material is a tampon and said holder is shaped for vaginal insertion.

7. The device of claim 3 wherein said retaining structure is an elongate tube.

8. The device of claim 7 wherein said tube extends from said head portion to the second end of said holder.

9. The device of claim 3 wherein the retaining structure is a ring or C-shaped member disposed adjacent the enlarged head portion to retain the material when the plunger tube is withdrawn.

10. The device of claim 5 wherein said stop is a ring or C-shaped member disposed near the second end of the tubular holder, and said raised area is a ring or C-shaped member extending from the outer surface of the tubular plunger, distally of its expulsion end.

11. The device of claim 1 or 3 wherein a portion of one end of the retaining structure is folded under, and the tubular plunger includes a plurality of petals at its first end, at least one of which is folded back for engagement with said folded under portion to retain the tubular plunger within the tubular holder when the plunger is withdrawn prior to use.

12. The device of claim 1 wherein said retaining structure has a thickness of from about 0.005" to 0.022".

13. The device of claim 1 wherein the outer surface of the plunger is spaced from the inner surface of the retaining tube by about 0.004" to 0.015".

14. The device of claim 1 wherein the retaining structure includes at least one portion which extends radially inwardly and is disposed circumferentially at an end of said retaining structure.

15. The device of claim 14 wherein said portion is a crimp.

16. The device of claim 15 wherein said retaining structure includes at least three circumferentially spaced crimps.

* * * * *